(12) United States Patent
Goldie

(10) Patent No.: US 7,641,334 B1
(45) Date of Patent: Jan. 5, 2010

(54) EARPLUG APPARATUS

(76) Inventor: Gregory A Goldie, 32 Patsy's Flat Road, P.O. Box 151, Pacific Palms, NS (AU) NSW 2428

( * ) Notice: Subject to any disclaimer, the term of this patent is extended or adjusted under 35 U.S.C. 154(b) by 0 days.

(21) Appl. No.: 12/241,986

(22) Filed: Sep. 30, 2008

(51) Int. Cl.
*G02C 5/20* (2006.01)

(52) U.S. Cl. .................. 351/123; 351/158; 128/864; 128/866

(58) Field of Classification Search .......... 351/123, 351/122, 121, 111, 158, 118, 119, 41; 2/454, 2/12, 13, 426; 128/864, 866, 867, 868, 857, 128/858; D16/315, 306, 325
See application file for complete search history.

(56) References Cited

U.S. PATENT DOCUMENTS

| 3,856,007 | A | | 12/1974 | Leight | |
|---|---|---|---|---|---|
| 3,970,082 | A | * | 7/1976 | Leight | ............ 128/866 |
| D262,491 | S | | 12/1981 | Ebert | |
| 5,133,596 | A | | 7/1992 | Korny et al. | |
| 5,475,449 | A | | 12/1995 | Pyle | |
| 5,703,670 | A | * | 12/1997 | Callard | ............ 351/123 |
| 5,806,526 | A | | 9/1998 | Rhoad | |
| 5,809,574 | A | * | 9/1998 | Falco et al. | ............ 2/209 |
| D426,845 | S | | 6/2000 | Green et al. | |
| 6,382,213 | B1 | * | 5/2002 | Sanpei | ............ 128/864 |
| 6,728,974 | B2 | | 5/2004 | Wadsworth | |
| 7,133,532 | B2 | | 11/2006 | Rickards | |
| 7,213,916 | B1 | | 5/2007 | Pettett | |
| D561,233 | S | * | 2/2008 | McLaughlin | ............ D16/315 |

* cited by examiner

*Primary Examiner*—Hung X Dang
(74) *Attorney, Agent, or Firm*—Crossley Patent Law; Mark A. Crossley

(57) ABSTRACT

The ear protection apparatus is provided as ear protection with various means of attachment to existing eyeglasses and also as ear protection including eyeglasses. Various embodiments provide multiple means for multiply adjustable positioning of the ear protection. Multiple plane adjustments are provided, with flex tubes with memory comprising a part of those adjustments. Refined earplug design provides for relaxed fit to a variety of ear sizes and shapes.

18 Claims, 7 Drawing Sheets

EARPLUG APPARATUS

BACKGROUND OF THE INVENTION

Safety equipment for eyes and ears has become more important daily in countless situations and especially in work environments. Governmental and insurance regulations have reinforced that importance. Safety glasses and earplugs are therefore well known. More recently, devices combining safety glasses and earplugs have been proposed. These combinations can do away with the clumsy separate eye and ear protection devices which are less than user friendly. Problems with these proposed devices remain, though, and include means for attachment to glasses, poor ear fit, difficult ear plug alignment, excessive temple and ear tension, lack of component memory, and limited adjustability. All of these problems easily result in a lack of use of eye and ear protection. The present apparatus successfully solves these problems and more.

FIELD OF THE INVENTION

The ear protection apparatus relates to safety glasses and earplugs and more especially to an ear protection apparatus which attaches to eyeglasses and provides various temple bar attachment means combined with multiple means for adjustably positioning earplugs.

SUMMARY OF THE INVENTION

The general purpose of the ear protection apparatus, described subsequently in greater detail, is to provide a ear protection apparatus which has many novel features that result in an improved ear protection apparatus which is not anticipated, rendered obvious, suggested, or even implied by prior art, either alone or in combination thereof.

To attain this, the ear protection apparatus is provided with both ear protection and eyeglasses together or as ear protection fitted to existing eyeglasses. A plurality of attachment means for attaching ear protection to eyeglasses is provided. A plurality of swivel and pivot planes for ear protection adjustment is provided, in various embodiments. Ear protection may be worn either in front of or behind a user's ears. The flex tubes with memory, used on each side of the temple bars and pads of each embodiment provide for selective shape retention. Sophisticated earplug design provides for fit to virtually any size and shape of ears, without excessive tension placed on the ears.

Thus has been broadly outlined the more important features of the improved ear protection apparatus so that the detailed description thereof that follows may be better understood and in order that the present contribution to the art may be better appreciated.

An object of the present apparatus is to provide an ear protection apparatus which removably fits to existing eyeglasses.

Another object of the ear protection apparatus is to include eyeglasses.

An added object of the ear protection apparatus is to provide multiple means for attachment to eyeglasses.

Another object of the ear protection apparatus is to provide multiple adjustments for fitting the ears of a user.

A further object of the ear protection apparatus is to provide for selective movement of earplugs away from a user's ears.

An added object of the ear protection apparatus is to prevent excessive pressure on a user's head while providing ear protection.

And, an object of the ear protection apparatus is to fit in front of and behind a user's ears.

These together with additional objects, features and advantages of the improved ear protection apparatus will be readily apparent to those of ordinary skill in the art upon reading the following detailed description of presently preferred, but nonetheless illustrative, embodiments of the improved ear protection apparatus when taken in conjunction with the accompanying drawings.

In this respect, before explaining the current embodiments of the improved ear protection apparatus in detail, it is to be understood that the ear protection apparatus is not limited in its application to the details of construction and arrangements of the components set forth in the following description or illustration. Those skilled in the art will appreciate that the concept of this disclosure may be readily utilized as a basis for the design of other structures, methods, and systems for carrying out the several purposes of the improved ear protection apparatus. It is therefore important that the claims be regarded as including such equivalent constructions insofar as they do not depart from the spirit and scope of the ear protection apparatus. It is also to be understood that the phraseology and terminology employed herein are for purposes of description and should not be regarded as limiting.

DETAILED DESCRIPTION OF THE DRAWINGS

With reference now to the drawings, and in particular FIGS. 1 through 9 thereof, the principles and concepts of the ear protection apparatus embodiments generally designated by the reference number 10, and more specifically to numbers 10A, 10B, 10C, 10D, 10E, 10F, 10G, and 10H will be described.

Referring to FIGS. 1-9, it is important to note that the apparatus 10 is provided both for fit to existing eyeglasses 80 or as a combination of ear protection and eyeglasses 80.

Figure 1:
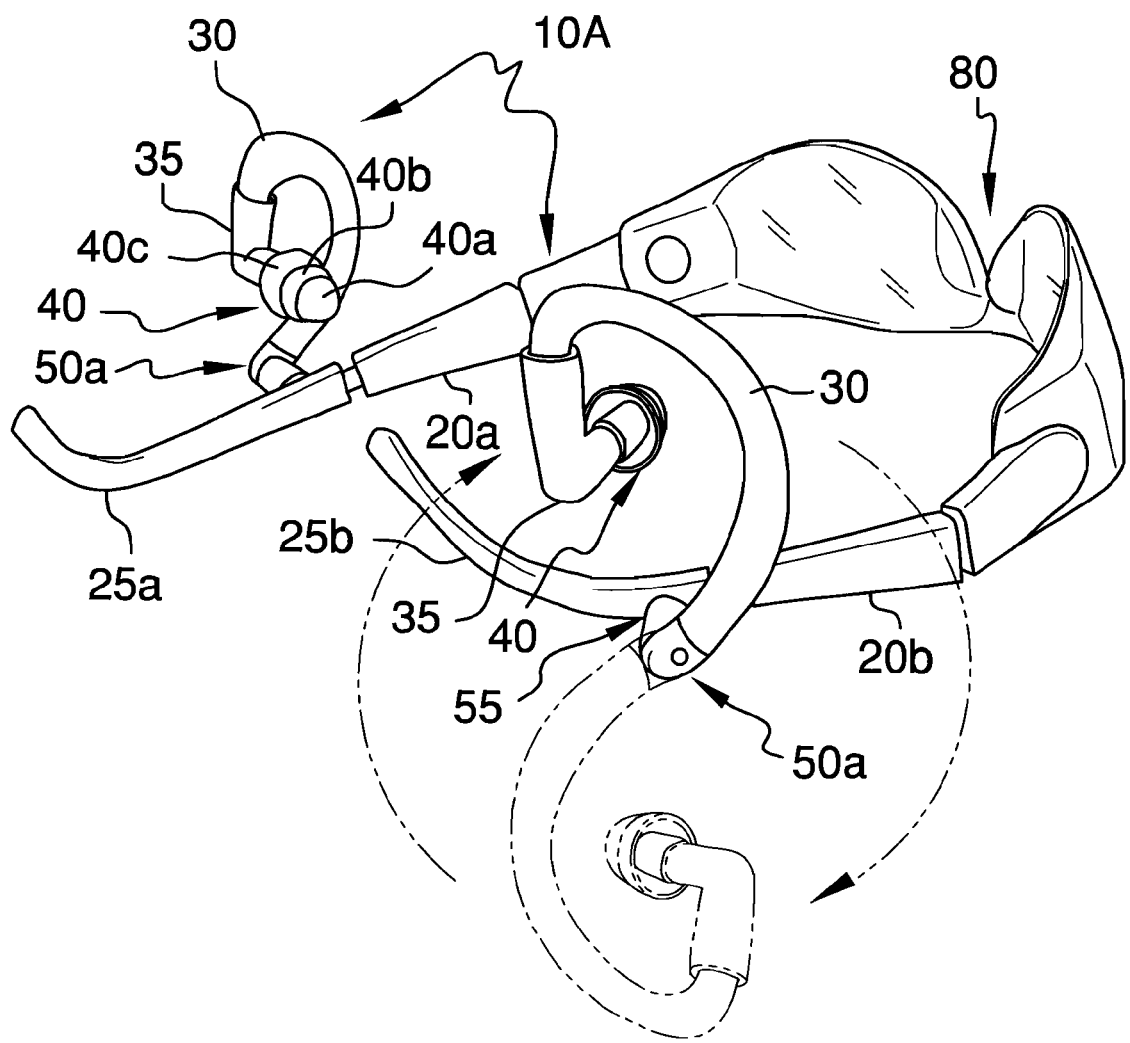
FIG. 1 is a perspective view of one embodiment of the apparatus.
Figure 1A:
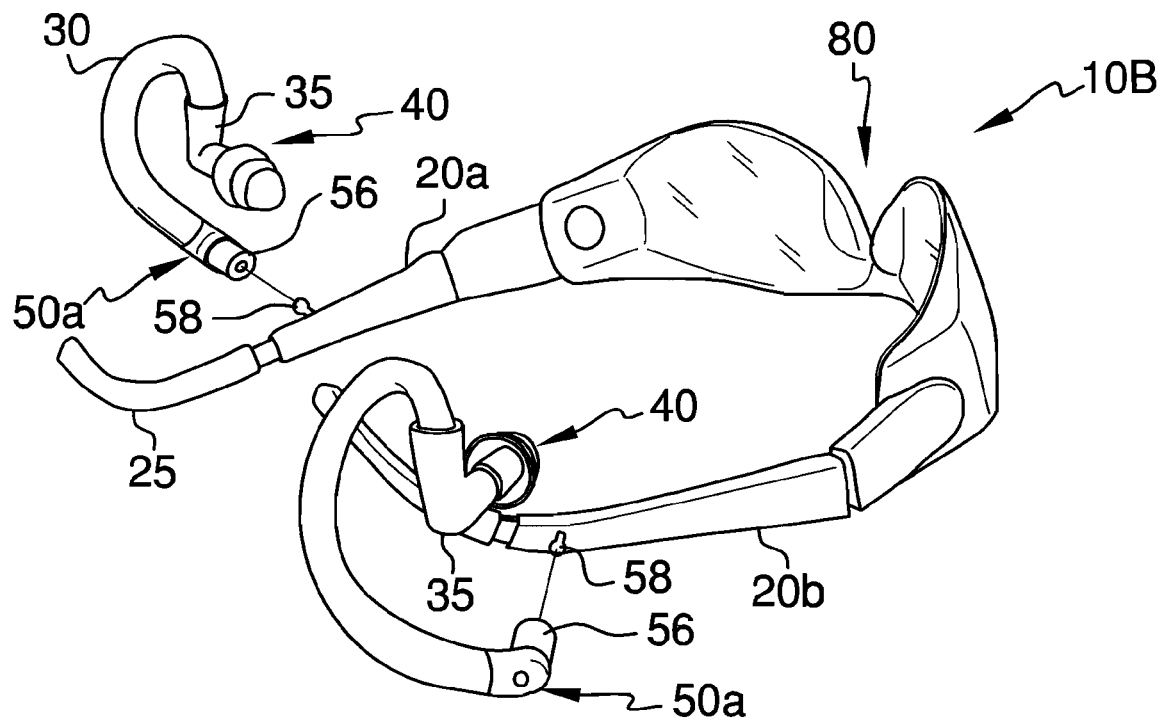
FIG. 1A is a perspective view of an alternate embodiment of the apparatus.
Figure 2:
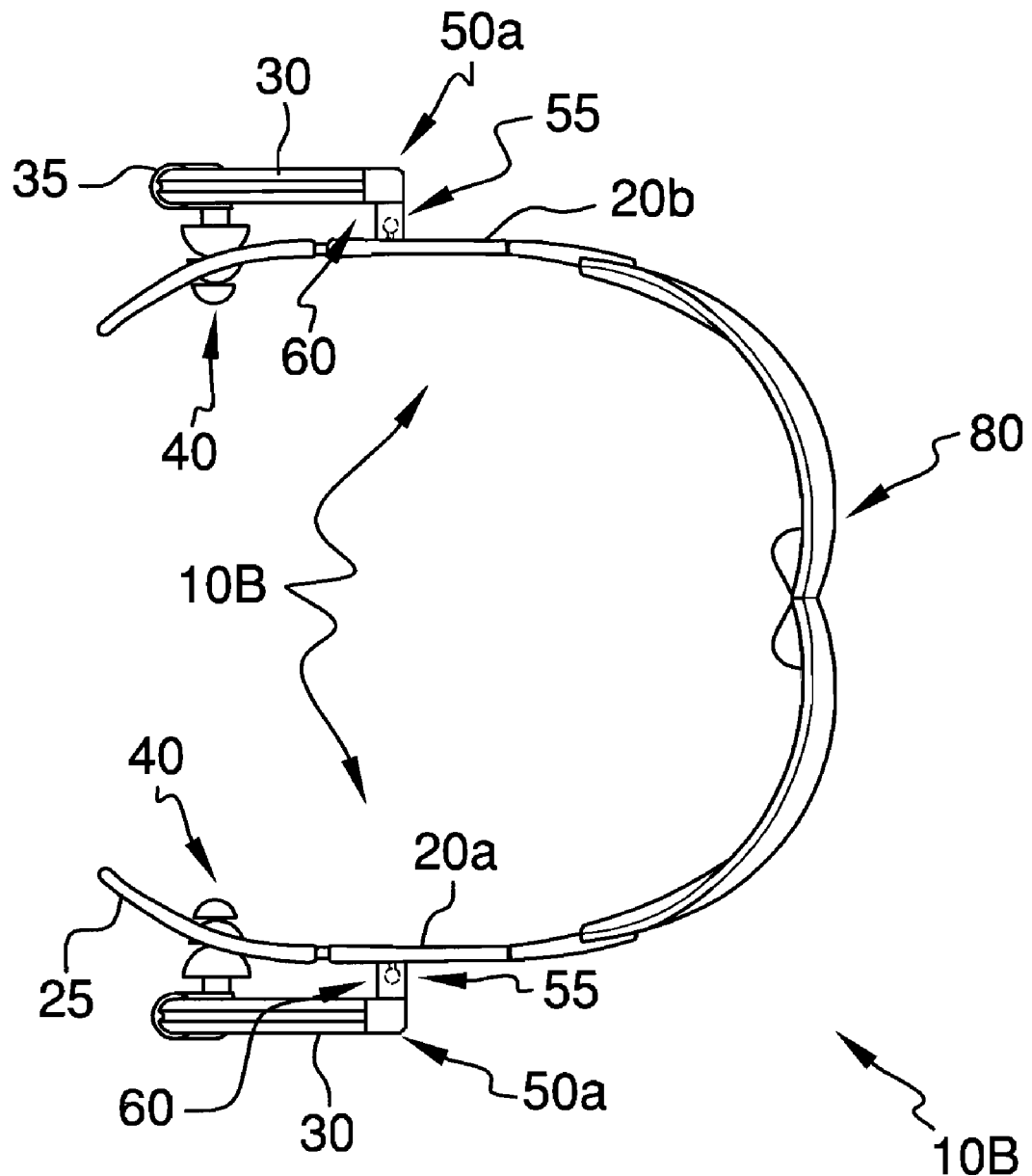
FIG. 2 is a top plan view of the embodiment of FIG. 1A

Referring to FIGS. 1, 1A, and 2, the ear protection apparatus 10A and 10B illustrate like components with the exception of the temple members which are comprised of either right temple pad 25*a* and left temple pad 25*b* or right temple bar 20*a* and left temple bar 20*b*. FIG. 1 illustrates the use of right temple pad 25*a* and left temple pad 25*b*. FIGS. 1A and 2 illustrate the use of right temple bar 20a and left temple bar 20b. The temple members of each of FIGS. 1, 1A, and 2 are attached to a ball and socket 55. Each temple member is removably fitted to eyeglasses 80, and each temple member is optionally included with the eyeglasses 80. Each ball and socket provides 360 of movement between the ball 58 and the socket 56. The ball 58 is dis-connectable from the socket 56. A first swivel 50a is affixed to each ball and socket 55. Each first swivel 50a has at least 180 degrees of pivot. The important clearance 60 of about 8 millimeters provided between each first swivel 50a and each temple member provides for the ball and sockets 55 to be fitted either in front of or behind a user's ears, depending upon the positioning of various embodiments of the temple members. A flex tube 30 is affixed to each first swivel 50a. Each flex tube 30 provides flexible movement with memory, such that the positional arrangement of each flex tube 30 is held until changed by a user. An angle member 35 is affixed to an end of each flex tube 30 opposite the first swivel 50a. Each angle member 35 can rotate 360 degrees about flex tube 30. The angle of each angle member 35 is about 90 degrees, but not relegated to only that, depending upon the embodiment. An earplug 40 is affixed to each angle member 35. Each earplug 40 comprises a plurality of pliable conical plugs, each conical plug having a diameter. The plugs comprise the third plug 40c most proximal to the angle member 35.

The second plug 40b is affixed to the third plug 40c. The diameter of the second plug 40b is less than the diameter of the third plug 40c. The first plug 40a is affixed to the second plug 40b. The first plug has a diameter less than the diameter of the second plug 40b. The earplug 40 design is important in providing comfortable fit to a variety of ear shapes and sizes, without each earplug 40 having to be tightly tensioned against an ear.

Figure 3:
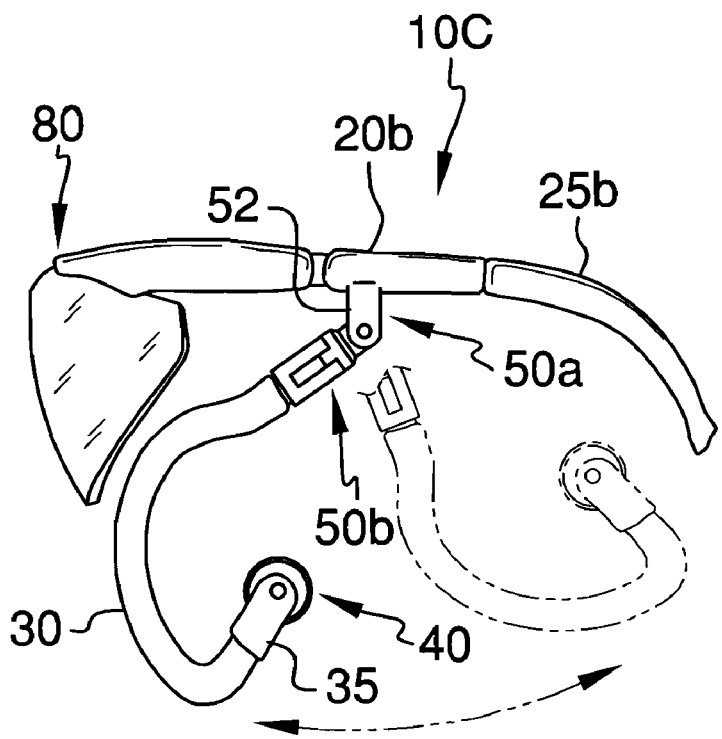
FIG. 3 is a lateral elevation view of an alternate embodiment of the apparatus.
Figure 4:
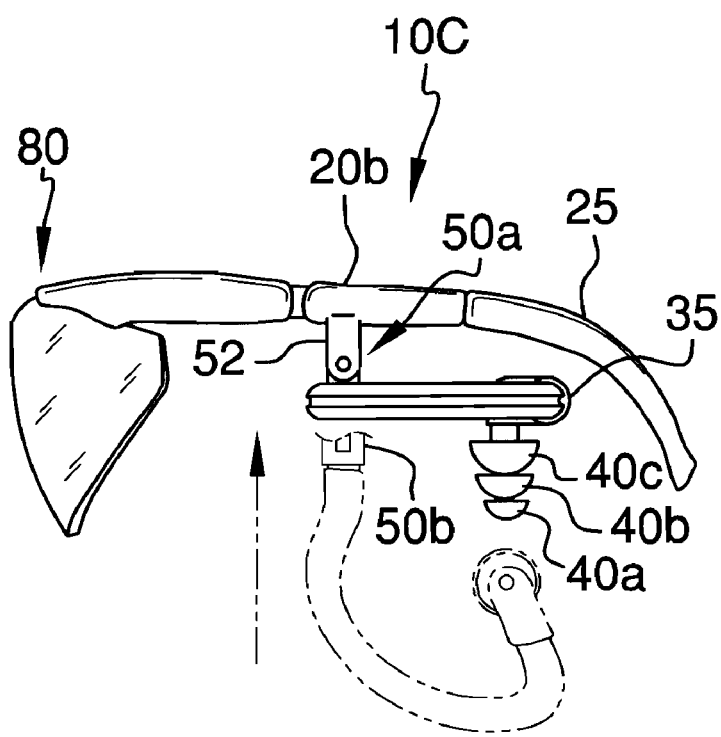
FIG. 4 is a lateral elevation of the embodiment of FIG. 3, the swivels in an alternately pivoted position.

Referring to FIGS. 3 and 4, the embodiment 10C illustrates dual swivels which are used on left temple bar 20b and right temple bar 20a (not shown). A first swivel 50a is affixed to each temple member via a downwardly disposed arm 52. The pivot of the first swivel 50a is in a plane paralleling the substantially horizontal plane of each temple member. The first swivel 50a has at least 180 degrees of pivot. A second swivel 50b is affixed to the first swivel 50a. Each second swivel 50b has a pivot perpendicular to the substantially horizontal plane of the temple members. Each second swivel 50b has at least 180 degrees of pivot. A flex tube 30 with memory is affixed to each second swivel 50b. An angle member 35 is affixed to an end of each flex tube 30 opposite the second swivel 50b. An earplug 40 is affixed to each angle member 35. Each earplug 40 is identical to those of FIGS. 1, 1A, and 2.

Figure 5:
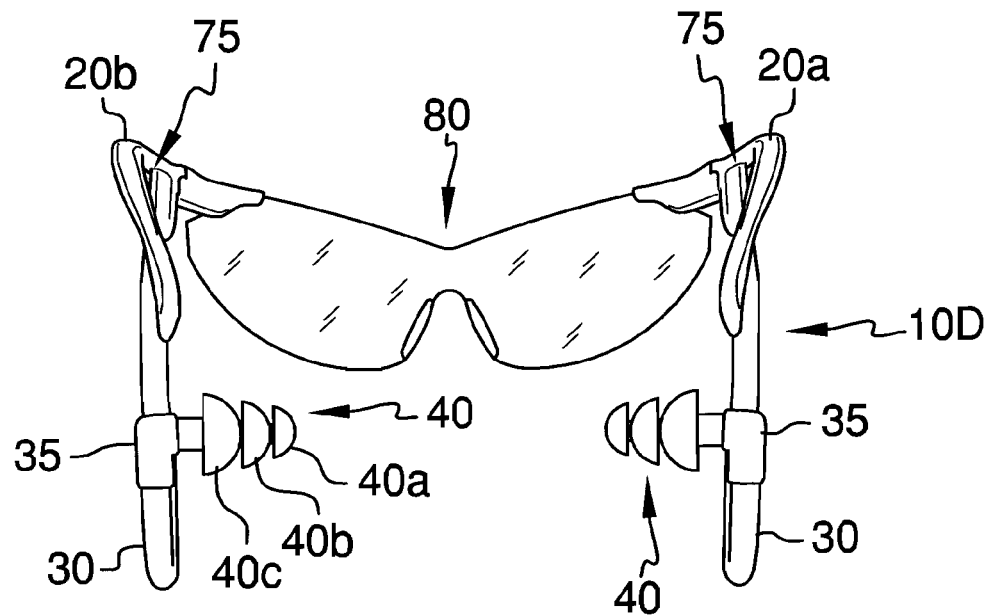
FIG. 5 is a rear perspective view of an alternate embodiment of the apparatus.

Referring to FIG. 5, the apparatus 10D is removably affixed to a pair of eyeglasses 80. An alligator clip 75 is attached to the right temple bar 20a and left temple bar 20b, respectively. A flex tube with memory 30 is affixed to each temple member.

An angle member 35 is affixed to each flex tube 30 at an end opposite the alligator clip 75. An earplug 40 is affixed to each angle member 35. The earplugs 40 are identical to those of embodiments 10A, 10B, and 10C.

Figure 6:
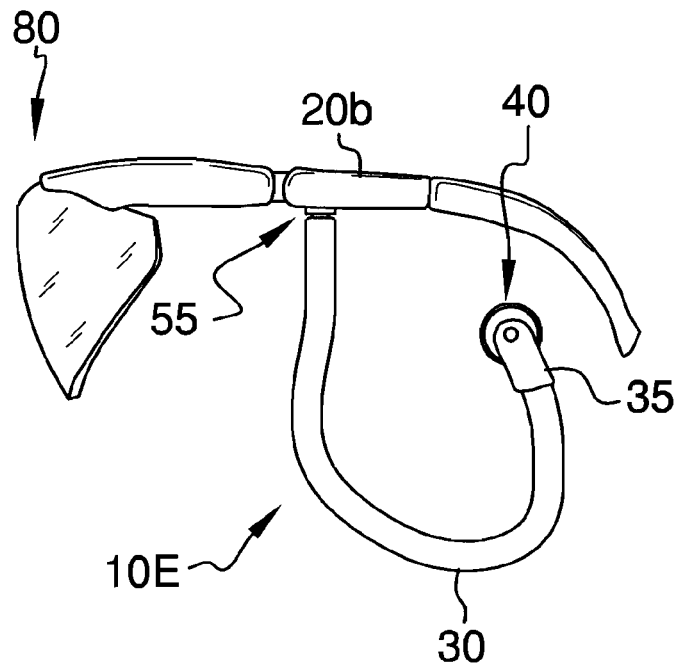
FIG. 6 is a lateral elevation view of an alternate embodiment of the apparatus.

Referring to FIG. 6, the embodiment 10E uses right temple bar 20a (not shown) and left temple bar 20b. A ball and socket 55 is attached to a lower portion of each temple member. Each ball 58 is removably fitted to each socket 56. A flex tube with memory 30 is affixed to each ball and socket 55. An angle member 35 is affixed to the end of each flex tube opposite the ball and socket 55. Earplugs 40 are affixed to the angle members. Earplugs 40 identical to those of embodiments 10A, 10B, 10C, and 10D are used for the same reasons.

Figure 8:
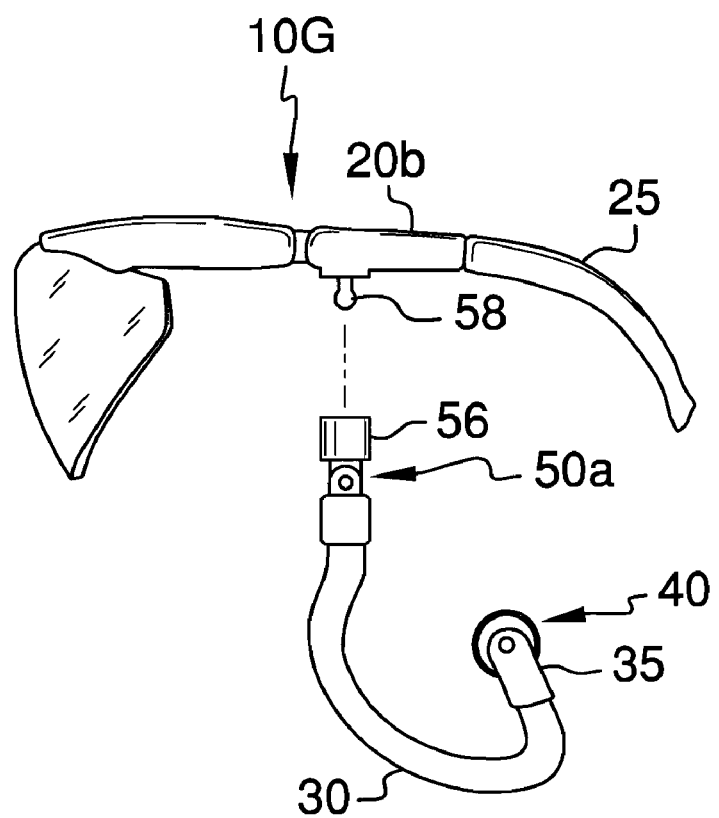
FIG. 8 is a lateral elevation view of an alternate embodiment of the apparatus.

Referring to FIG. 8, the embodiment 10G uses left temple bar 20b and right temple bar (not shown) 20a. A ball and socket 55 is attached to a lower portion of each temple member. Each ball 58 is removably fitted to each socket 56. A first swivel 50a is attached to each ball and socket 55. With 360 degrees of movement of the ball and socket 55 and at least 180 degrees of pivot of the first swivel 50a yields almost limitless adjustability in positioning the flex tube 30 as desired. An angle member 35 is affixed to the end of each flex tube opposite the first swivel 50a. An earplug 40 is affixed to each angle member 35. Earplugs 40 identical to those of embodiments 10A, 10B, 10C, and 10D are used for the same reasons.

Figure 7:
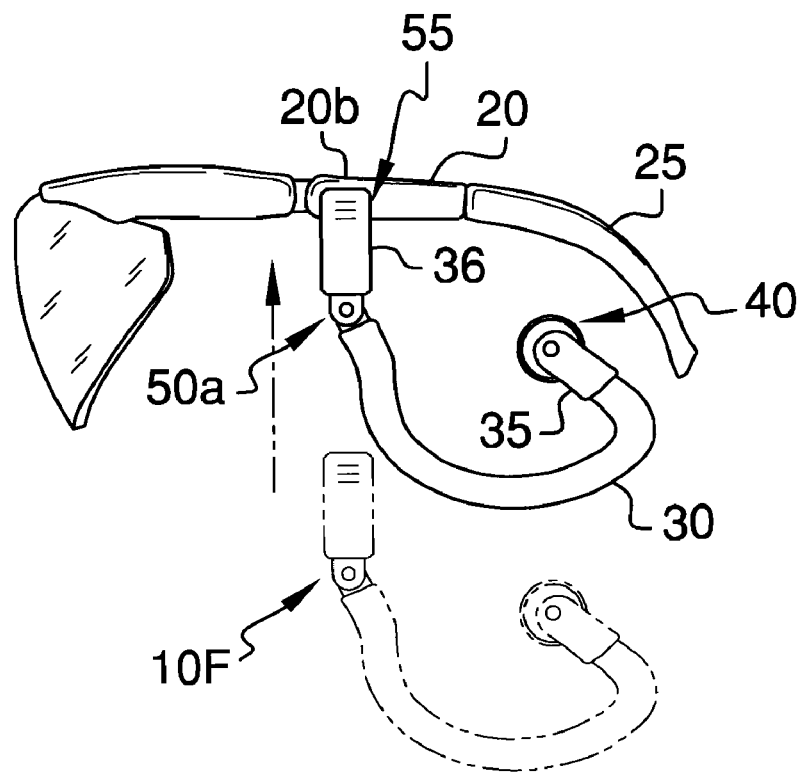
FIG. 7 is a lateral elevation view of an alternate embodiment of the apparatus.

Referring to FIG. 7, temple bar 20b and temple bar 20a (not shown) are used. A ball and socket 55 with dis-connectable ball 58 and socket 56 is disposed outwardly on each temple member. A right angle member 36 is fitted with the socket 56. A first swivel 50a is fitted to a bottom of each right angle member 36. A flex tube 30 is affixed to each first swivel 50a. An angle member 35 is affixed to each flex tube 30 at the end opposite the first swivel 50a. An earplug 40 is affixed to each angle member 35. Earplugs 40 identical to the other embodiments of the apparatus 10 are used for the same reasons.

Figure 9:
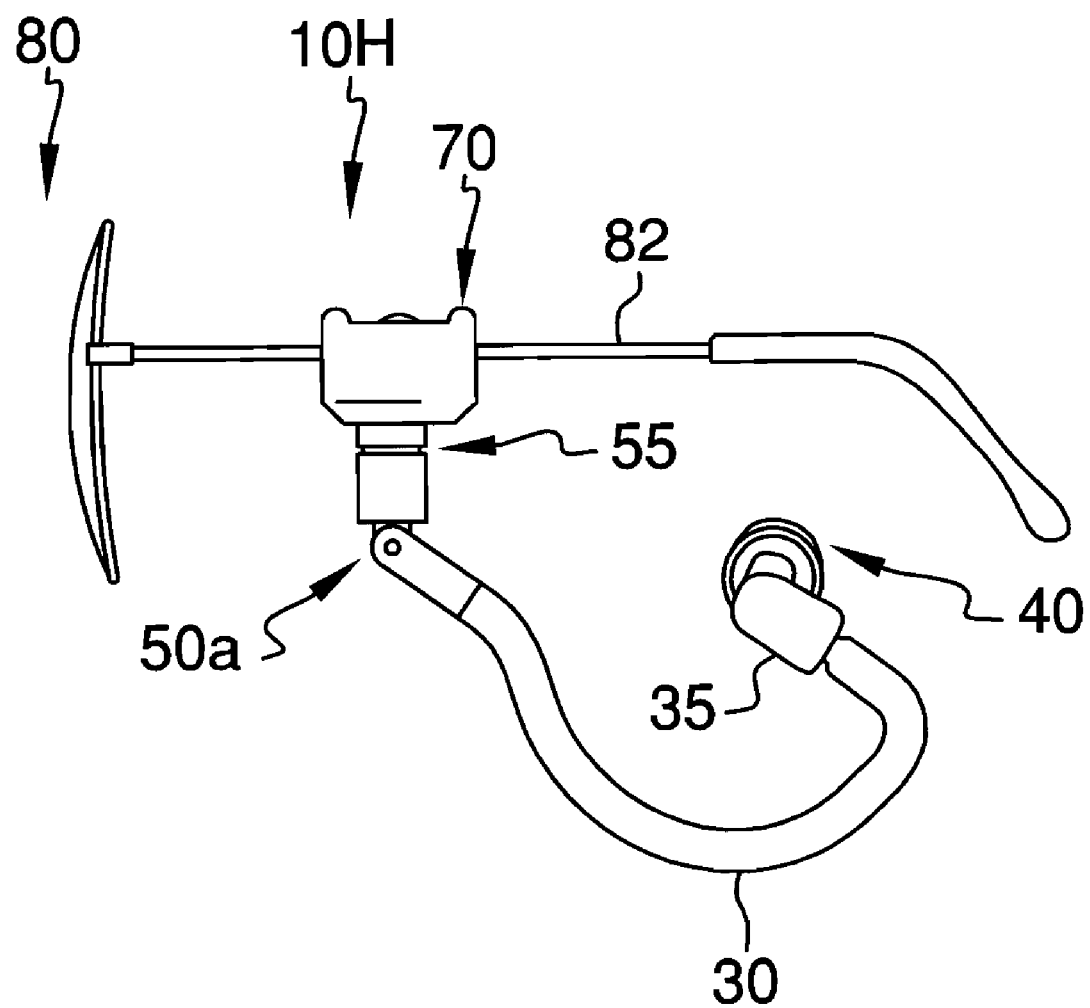
FIG. 9 is a lateral elevation view of an alternate embodiment of the apparatus.

Referring to FIG. 9, a clipover 70 is used on each existing temple bar 82 of existing eyeglasses 80. Each clipover 70 is fitted with a ball and socket 55 at a bottom of the clipover 70. A first swivel 50a is affixed to each ball and socket 55. A flex tube 30 is affixed to each first swivel 50a. An angle member 35 is affixed to each flex tube 30 at the end opposite the first swivel 50a. Earplugs 40 identical to those of the other embodiments of the apparatus 10 are affixed to the angle members 35 for identical reasons.

With respect to the above description then, it is to be realized that the optimum dimensional relationships for the parts of the ear protection apparatus, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the ear protection apparatus.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the ear protection apparatus may be used.

Therefore, the foregoing is considered as illustrative only of the principles of the ear protection apparatus. Further, since numerous modifications and changes will readily occur to those skilled in the art, it is not desired to limit the ear protection apparatus to the exact construction and operation shown and described, and accordingly, all suitable modifications and equivalents may be resorted to, falling within the scope of the ear protection apparatus.

What is claimed is:

1. An ear protection apparatus, comprising:
   a pair of temple members comprising a right temple member and a left temple member, each temple member fitted to an eyeglasses;
   a flex tube with memory affixed to each temple member;
   means for 360 degrees of selective movement between the flex tube and the temple member;
   an angle member affixed to an end of each flex tube opposite the temple member;

an earplug affixed to each angle member, each earplug comprising a plurality of pliable conical plugs, each conical plug having a diameter, the plugs comprising:
  a third plug most proximal to the angle member;
  a second plug affixed to the third plug, the diameter of the second plug less than the diameter of the third plug;
  a first plug affixed to the second plug, the diameter of the first plug less than the diameter of the second plug.

2. The apparatus according to claim 1 wherein each temple member is further removably fitted to eyeglasses.

3. The apparatus according to claim 2 wherein each temple member further comprises a temple pad.

4. The apparatus according to claim 3 wherein the means for 360 degrees of selective movement between the flex tube and the temple member further comprises a ball dis-connectable from a socket.

5. The apparatus according to claim 2 wherein each temple member further comprises a temple bar.

6. The apparatus according to claim 5 wherein the means for 360 degrees of selective movement between the flex tube and the temple member further comprises a ball dis-connectable from a socket.

7. The apparatus according to claim 1 wherein each temple member further comprises a temple pad.

8. The apparatus according to claim 7 wherein the means for 360 degrees of selective movement between the flex tube and the temple member further comprises a ball dis-connectable from a socket.

9. The apparatus according to claim 1 wherein each temple member further comprises a temple bar.

10. The apparatus according to claim 9 wherein the means for 360 degrees of selective movement between the flex tube and the temple member further comprises a ball dis-connectable from a socket.

11. An ear protection apparatus, comprising:
  a pair of temple members comprising a right temple member and a left temple member, each temple member fitted to an eyeglasses;
  a disconnectable ball and socket affixed to each temple member;
  a swivel affixed to each ball and socket, the swivel having at least 180 degrees of pivot;
  a clearance of about 8 millimeters between the temple member and the swivel;
  a flex tube with memory affixed to each swivel;
  an angle member affixed to an end of each flex tube opposite the swivel;
  an earplug affixed to each angle member, each earplug comprising a plurality of pliable conical plugs, each conical plug having a diameter, the plugs comprising:
    a third plug most proximal to the angle member;
    a second plug affixed to the third plug, the diameter of the second plug less than the diameter of the third plug;
    a first plug affixed to the second plug, the diameter of the first plug less than the diameter of the second plug.

12. The apparatus according to claim 11 wherein the each temple member is further removably fitted to eyeglasses.

13. The apparatus according to claim 12 wherein each temple member further comprises a clipover removably fitted to eyeglasses.

14. The apparatus according to claim 12 wherein each temple member further comprises and alligator clip removably fitted to eyeglasses.

15. An ear protection apparatus, comprising:
  a pair of temple members comprising a right temple member and a left temple member, each temple member fitted to an eyeglasses;
  a first swivel affixed to each temple member, a pivot of the first swivel in a plane paralleling a substantially horizontal plane of each temple member, the first swivel having at least 180 degrees of pivot;
  a second swivel affixed to the first swivel, the second swivel having a pivot perpendicular to the substantially horizontal plane of the temple members, the second swivel having at least 180 degrees of pivot;
  a flex tube with memory affixed to each second swivel;
  an angle member affixed to an end of each flex tube opposite the second swivel;
  an earplug affixed to each angle member, each earplug comprising a plurality of pliable conical plugs, each conical plug having a diameter, the plugs comprising:
    a third plug most proximal to the angle member;
    a second plug affixed to the third plug, the diameter of the second plug less than the diameter of the third plug;
    a first plug affixed to the second plug, the diameter of the first plug less than the diameter of the second plug.

16. The apparatus according to claim 15 wherein the each temple member is further removably fitted to eyeglasses.

17. The apparatus according to claim 16 wherein each temple member further comprises a clipover removably fitted to eyeglasses.

18. The apparatus according to claim 16 wherein each temple member further comprises and alligator clip removably fitted to eyeglasses.

* * * * *